US011717360B2

(12) United States Patent
Krebs et al.

(10) Patent No.: US 11,717,360 B2
(45) Date of Patent: Aug. 8, 2023

(54) SYSTEMS AND METHODS FOR ROBOTIC INFECTION TREATMENT OF A PROSTHESIS

(71) Applicant: MAKO Surgical Corp., Fort Lauderdale, FL (US)

(72) Inventors: Viktor Krebs, Fort Lauderdale, FL (US); Peter Ebbitt, Fort Lauderdale, FL (US); Snehal Kasodekar, Weston, FL (US); Hyosig Kang, Weston, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 319 days.

(21) Appl. No.: 16/249,542

(22) Filed: Jan. 16, 2019

(65) Prior Publication Data

US 2019/0216559 A1 Jul. 18, 2019

Related U.S. Application Data

(60) Provisional application No. 62/618,189, filed on Jan. 17, 2018.

(51) Int. Cl.
*A61B 34/32* (2016.01)
*A61M 3/02* (2006.01)
(Continued)

(52) U.S. Cl.
CPC ........ *A61B 34/32* (2016.02); *A61B 17/22012* (2013.01); *A61B 34/10* (2016.02);
(Continued)

(58) Field of Classification Search
CPC ......... A61B 34/32; A61B 34/10; A61B 34/20; A61B 34/76; A61B 2034/2055;
(Continued)

(56) References Cited

U.S. PATENT DOCUMENTS 5,499,970 A 3/1996 Olson
6,033,415 A * 3/2000 Mittelstadt ............ G06T 3/0006
128/922

(Continued)

FOREIGN PATENT DOCUMENTS

WO WO-2008/040020 A2 4/2008

OTHER PUBLICATIONS

Bahls et al., Extending the Capability of Using a Waterjet in Surgical Interventions by the Use of Robotics, IEEE Transactions on Biomedical Engineering, vol. 64, No. 2, Feb. 2017, 11 Pages.

(Continued)

*Primary Examiner* — Kami A Bosworth
*Assistant Examiner* — Antarius S Daniel
(74) *Attorney, Agent, or Firm* — Foley & Lardner LLP

(57) ABSTRACT

A method for debriding an infected implant area using a robotic-assisted surgery system. The method includes determining, by a processing circuit associated with a computer, an area to be debrided, the debridement area including at least a surface of an implant or patient tissue, and generating, by the processing circuit, a plan for debriding the debridement area. The method further includes controlling a debridement tool, by the robotic-assisted surgery system, while the debridement tool is used to carry out the debridement plan, and monitoring the debridement by the processing circuit.

16 Claims, 6 Drawing Sheets

(51) Int. Cl.

| | | |
|---|---|---|
| | *A61B 34/00* | (2016.01) |
| | *A61N 5/06* | (2006.01) |
| | *A61B 34/20* | (2016.01) |
| | *A61F 2/46* | (2006.01) |
| | *A61B 17/22* | (2006.01) |
| | *A61B 34/10* | (2016.01) |
| | *A61B 90/80* | (2016.01) |
| | *A61B 34/30* | (2016.01) |
| | *A61B 18/18* | (2006.01) |
| | *A61B 17/00* | (2006.01) |
| | *A61F 2/30* | (2006.01) |
| | *A61N 7/00* | (2006.01) |

(52) U.S. Cl.
CPC .............. *A61B 34/20* (2016.02); *A61B 34/25* (2016.02); *A61B 34/30* (2016.02); *A61B 34/76* (2016.02); *A61B 90/80* (2016.02); *A61F 2/461* (2013.01); *A61M 3/0266* (2013.01); *A61N 5/0624* (2013.01); *A61B 2017/00115* (2013.01); *A61B 2017/00154* (2013.01); *A61B 2017/00203* (2013.01); *A61B 2017/00221* (2013.01); *A61B 2017/00889* (2013.01); *A61B 2018/1807* (2013.01); *A61B 2034/102* (2016.02); *A61B 2034/105* (2016.02); *A61B 2034/108* (2016.02); *A61B 2034/2055* (2016.02); *A61B 2034/2068* (2016.02); *A61B 2034/2074* (2016.02); *A61B 2034/252* (2016.02); *A61B 2034/254* (2016.02); *A61B 2217/007* (2013.01); *A61F 2002/30719* (2013.01); *A61F 2002/4632* (2013.01); *A61M 2202/0468* (2013.01); *A61N 2005/0626* (2013.01); *A61N 2005/0652* (2013.01); *A61N 2005/0661* (2013.01); *A61N 2007/0017* (2013.01)

(58) Field of Classification Search
CPC ........ A61B 2034/102; A61B 2034/105; A61B 2217/007; A61B 2218/001; A61B 2218/002; A61F 2/461; A61F 2002/30719; A61F 2002/4646; A61F 2002/467; A61F 2/4675; A61F 2/4657; A61M 3/0266; A61M 3/00; A61M 2250/0092; A61N 5/0624; A61N 2005/0626; A61N 2005/0661
See application file for complete search history.

(56) References Cited

U.S. PATENT DOCUMENTS

| | | | |
|---|---|---|---|
| 6,283,986 B1* | 9/2001 | Johnson | ............... A61N 5/0616 607/88 |
| 8,010,180 B2 | 8/2011 | Quaid et al. | |
| 9,119,655 B2* | 9/2015 | Bowling | ................ A61B 34/20 |
| 9,333,060 B2* | 5/2016 | Hunter | ................ A61C 17/024 |
| 9,399,298 B2 | 7/2016 | Kang | |
| 9,839,523 B1* | 12/2017 | Foran | .................... A61F 2/3859 |
| 2006/0142657 A1 | 6/2006 | Quaid et al. | |
| 2007/0135706 A1* | 6/2007 | Shimko | .................... A61B 6/12 600/411 |
| 2010/0170362 A1 | 7/2010 | Bennett et al. | |
| 2013/0060278 A1* | 3/2013 | Bozung | ............. A61B 17/3403 606/205 |
| 2014/0171963 A1* | 6/2014 | Bahls | .................... A61B 34/30 606/130 |
| 2015/0335343 A1* | 11/2015 | Hunter | ............. A61B 17/32037 606/170 |
| 2016/0206375 A1* | 7/2016 | Abbasi | .................... A61B 34/35 |
| 2018/0014891 A1 | 1/2018 | Krebs et al. | |

OTHER PUBLICATIONS

International Search Report and Written Opinion for International Application No. PCT/US2019/013804, dated Apr. 29, 2019, 19 pages.

* cited by examiner

SYSTEMS AND METHODS FOR ROBOTIC INFECTION TREATMENT OF A PROSTHESIS

CROSS-REFERENCE TO RELATED APPLICATIONS

This application claims the benefit of and priority to U.S. Provisional Patent Application No. 62/618,189, filed Jan. 17, 2018, which is hereby incorporated by reference in its entirety.

BACKGROUND

The present disclosure is related to infection treatments for a prosthetic component, and in particular, to robotic-assisted infection treatment of a prosthetic component implanted on a patient's anatomy.

Once implanted into a patient, prosthetic devices may sometimes become infected. For example, a biofilm, a community of bacteria in a structural matrix, may infect a prosthetic implant by adhering to the surface of the implant. If a prosthetic implant becomes infected, the first treatment step is to decide whether to remove the infected prosthetic implant, though in the case of an early infection, the prosthetic implant does not necessarily have to be removed. Instead, a thorough debridement of the infected implant and surrounding tissue can be performed by, for example, irrigating the area using an irrigation fluid such as bactericidal solutions, nanoparticle solutions, biofilm inhibiting agents, and/or antibiotics, using an ultrasonic debridement tool, and or using irradiation. The irrigation and debridement should penetrate and destroy, for example, biofilms adhered to the surface of the prosthetic implant, thereby disinfecting the implant.

SUMMARY OF THE INVENTION

One embodiment of the invention relates to a method for debriding an infected implant area using a robotic-assisted surgery system. The method includes determining, by a processing circuit associated with a computer, an area to be debrided, the debridement area including at least a surface of an implant or patient tissue, and generating, by the processing circuit, a plan for debriding the debridement area. The method further includes controlling a debridement tool while the debridement tool is used to carry out the debridement plan, and monitoring, by the processing circuit, the debridement.

Another embodiment of the invention relates to a system for debriding an infected implant area. The system includes a robotic system including an articulated arm and a debridement tool coupled to the articulated arm and a processing circuit including a processor and non-transitory machine readable media with instructions stored thereon. The processing circuit is configured to determine an area to be debrided, the debridement area including at least a surface of an implant or patient tissue, and generate a plan for debriding the debridement area. The processing circuit is further configured to control a debridement tool while the debridement tool is used to carry out the debridement plan, and monitor the debridement.

BRIEF DESCRIPTION OF THE FIGURES

The accompanying drawings, which are incorporated and constitute a part of this specification, illustrate several embodiments that, together with the description, serve to explain the principles and features of the present disclosure.

DETAILED DESCRIPTION

Figure 1:
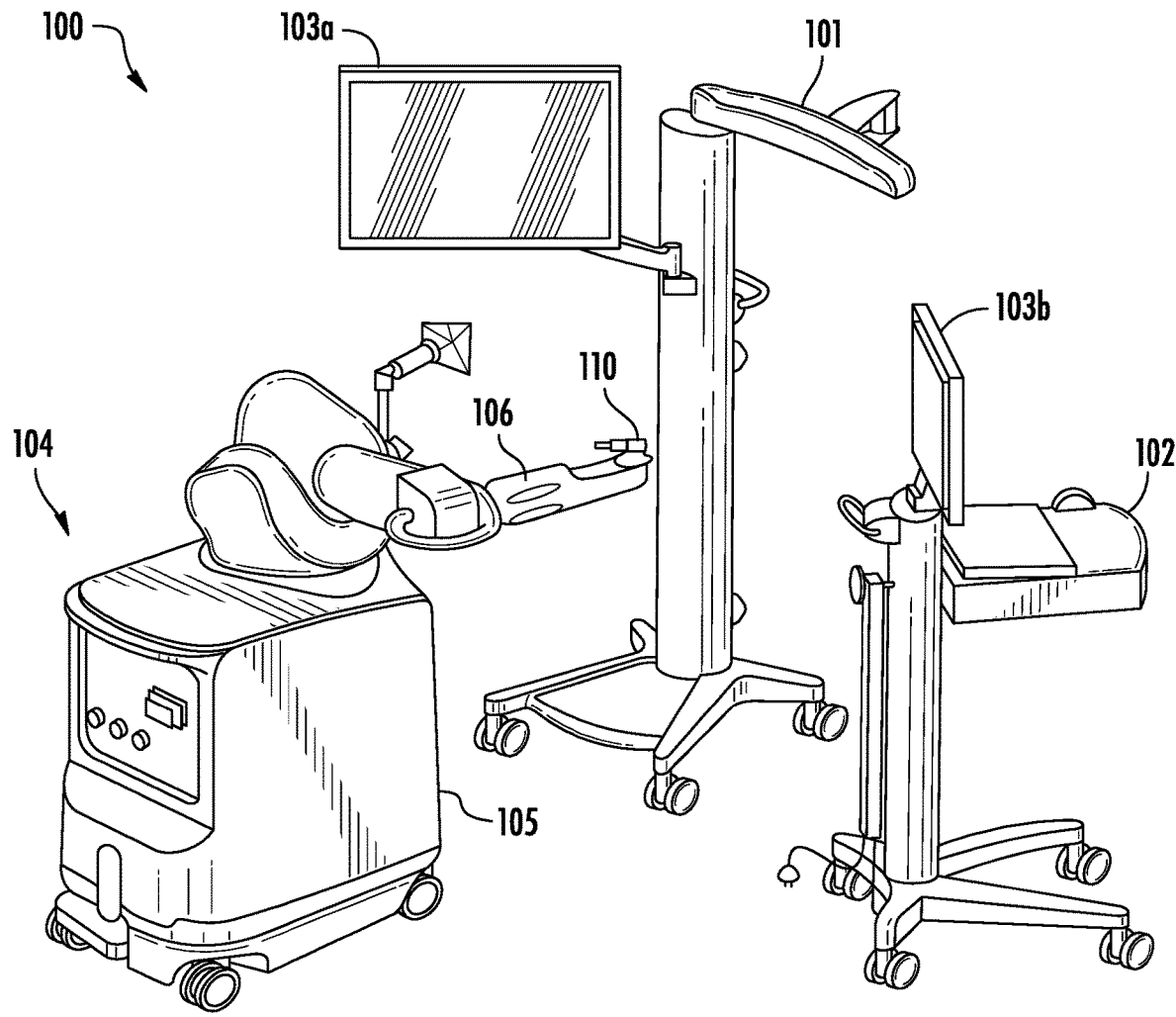
FIG. 1 illustrates a perspective view of a surgical system, according to an exemplary embodiment.

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

The present disclosure introduces a robotic-assisted approach to treating an implanted prosthetic device, such as a knee joint replacement or a hip joint replacement, by debriding the infected prosthesis and the surrounding tissue, such as by irrigation, ultrasonic debridement, irradiation to kill bacteria, or a combination thereof. With effective debridement of an infected prosthesis, early infections can be treated without the need for the prosthesis to be removed. Alternatively, more severe infections can be treated by removing the infected prosthesis, cleaning the infected prosthesis, and irrigating the infected patient tissues. In some embodiments, removal of the prosthesis can be carried out according to systems and methods described in U.S. application Ser. No. 15/649,416 filed Jul. 13, 2017 and entitled "Systems and Methods for a Robotic-Assisted Revision Procedure," which is incorporated herein in its entirety.

While implant and tissue debridement can be done manually by a practitioner, manual debridement relies on the practitioner's ability to cover the entire infected area. By contrast, the systems and methods described herein provide several technical advantages over existing debridement processes. For one, a practitioner using the robotic-assisted system described herein to irrigate an infected implant and/or tissue can use the robotic-assisted system to generate a debridement plan for covering all affected surfaces with an irrigation fluid, such as bactericidal solutions, nanoparticle solutions, biofilm inhibiting agents, and/or antibiotics. Further, the robotic-assisted system is able to assist the practitioner in carrying out the plan, or autonomously carry out the plan, as well as monitor the irrigation to confirm that even difficult-to-reach surfaces receive at least a minimum amount of debridement (e.g., which decreases the risk of leaving a portion of biofilm on the infected implant or leaving a portion of infected tissue untreated). Furthermore, the robotic-assisted system may be used to generate and implement a debridement plan using an ultrasonic tool for removing tissue from an implant component using robotic-assistance or autonomously. Finally, debridement can be planned for irradiation to kill bacteria on the implant. The debridement plans and process described herein may involve irrigation, ultrasonic debridement, irradiation, or any combination thereof.

Though the present disclosure makes reference to the knee and hip joints, and treating infected implants and surrounding tissues for the knee and the hip joints, the systems and methods disclosed herein are equally applicable to infected implants for other bones or joints and their surrounding tissues. For example, the systems and methods disclosed herein may be used with implants for the shoulder, the wrist, the spine, the ankle, etc. The systems and methods disclosed herein are suitable for the debridement of any implantable metallic device which may be used in any arthroplasty procedure and which may use any trauma fixation hardware.

Exemplary Robotic System

Various features of a robotic-assisted system and methods for debriding an infected implant and/or surrounding tissue according to the present disclosure will now be described in greater detail. FIG. 1 provides a schematic diagram of an exemplary computer-assisted surgery (CAS) system 100, in which processes and features associated with certain disclosed embodiments may be implemented. CAS system 100 may be configured to perform a wide variety of orthopedic surgical procedures (e.g., implantation and revision procedures), as well as other implant-related procedures such as the debridement procedures described herein. CAS system 100 includes a navigation system 101, a computing system 102, one or more display devices 103a and 103b, and a robotic system 104.

Robotic system 104 can be used in an interactive manner by a practitioner, such as a surgeon, to perform a procedure on a patient. As an example, the surgeon can use the robotic system 104 to make incisions such that the practitioner can access an infected implant. As another example, the surgeon can use the robotic system 104 to debride the infected implant, as well as the tissue surrounding the infected implant. As shown in FIG. 1, robotic system 104 includes a base 105, and an articulated arm 106. A surgical tool 110 is coupled to one end of the articulated arm 106. The surgical tool 110 may be, for example, an end effector having an operating member (e.g., a saw reamer or a burr) or is, in some embodiments, a debridement tool such as an irrigation tool (e.g., a pulsatile lavage hydro jet), an ultrasonic debridement tool, or an irradiation tool. The surgeon can manipulate the surgical tool 110 by grasping and manually moving the articulated arm 106 and/or the surgical tool 110. Alternatively, the surgeon can manipulate the surgical tool 110 by using an input/output device (not shown) to move the articulated arm 106 and/or the surgical tool 110 (e.g., by using a keyboard, a joystick, etc. to move the articulated arm 106 and/or the surgical tool 110).

Some embodiments of the robotic system 104 may further include a force system and a controller configured to provide a restraint guide. For example, the robotic system 104 may provide a restraint guide to aid a surgeon in preparing a bone to receive an implant or debriding an infected implant. The restraint guide may operate by providing control or guidance to the surgeon during manipulation of the surgical tool 110. When providing a restraint guide, the force system is configured to provide at least some force to the surgical tool 110 via the articulated arm 106, and the controller is programmed to generate control signals for controlling the force system. In one embodiment, the force system includes actuators and a back-drivable transmission that provide haptic (or force) feedback to constrain or inhibit the surgeon from manually moving the surgical tool 110 beyond predefined haptic boundaries defined by haptic objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. The force system and controller may be housed within the robotic system 104. In some embodiments, a handheld robot can be used, such as described in U.S. Pat. No. 9,399,298 and U.S. Patent Publication No. 2013/0060278, both of which are herein incorporated by reference in their entirety.

Navigation system 101 is configured to determine a pose (i.e., position and orientation) of one or more objects during a surgical procedure to detect movement of the object(s). For example, the navigation system 101 may include a detection device (e.g., an optical tracking device or a mechanical tracking device) that obtains a pose of an object with respect to a coordinate frame of reference of the detection device. As an object moves in the coordinate frame of reference, the detection device tracks the pose of the object to detect (or enable the CAS system 100 to determine) movement of the object. Additionally, by using the navigation system 101, the computing system 102 can capture data in response to movement of tracked object or objects. Tracked objects may include, for example, tools/instruments (e.g., the surgical tool 110), patient anatomy, implants/prosthetic devices, and components of the CAS system 100.

The navigation system 101 may be any navigation system that enables the CAS system 100 to continually determine (or track) a pose of the relevant anatomy of the patient or movement of surgical tool 110. For example, the navigation system 101 may include a non-mechanical tracking system, a mechanical tracking system, or any combination of non-mechanical and mechanical tracking systems suitable for use in a surgical environment. A mechanical tracking system may include a mechanical arm having passive joints for tracking and characterizing movement of the tracked object relative to a reference point. A non-mechanical tracking system may include an optical (or visual), magnetic, radio, or acoustic tracking system. Such systems typically include a detection device adapted to locate, in predefined coordinate space, specially recognizable trackable elements (or trackers) that are detectable by the detection device and that are either configured to be attached to an object to be tracked or are an inherent part of an object to be tracked. For example, a trackable element may include an array of markers having a unique geometric arrangement and a known geometric relationship to the tracked object when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers.

The markers may include any known marker, such as, for example, extrinsic markers (or fiducials) and/or intrinsic features of the tracked object. Extrinsic markers are artificial objects that are attached to the patient and/or other objects to be tracked (e.g., markers affixed to skin, markers implanted in bone, stereotactic frames, etc.). Extrinsic markers designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well-known. For example, an optical tracking system having a stationary stereo camera pair sensitive to infrared radiation may be used to track markers that emit infrared radiation either actively (such as a light emitting diode ("LED")) or passively (such as a spherical marker with a surface that reflects infrared radiation). As another example, a magnetic tracking system may include a stationary field generator that emits a spatially varying magnetic field sensed by small coils integrated into the tracked object.

Using pose data from the navigation system 101, the CAS system 100 (e.g., via the computing system 102 or via a computer of the navigation system 101) is also able to register, map, or coordinates in one space to those in another to achieve spatial alignment or correspondence (e.g., using a coordinate transformation process as is well-known). Objects in physical space may be registered to any suitable coordinate system, such as a coordinate system being used by a process running on a surgical controller and/or a computer device of the robotic system 104. For example, utilizing pose data from the navigation system 101, the CAS system 100 is able to associate the physical anatomy, such as the patient's tibia, with a representation of the anatomy (e.g., an image displayed on the display device 103). Based on tracked object and registration data, the CAS system 100 may determine, for example, a spatial relationship between the image of the anatomy and the relevant anatomy.

The CAS system 100 (e.g., via the computing system 102 or via a computer of the navigation system 101) may also include a coordinate transform process for mapping (or transforming) coordinates in one space to those in another in order to achieve spatial alignment or correspondence. For example, the CAS system 100 may use the coordinate transform process to map positions of tracked objects (e.g., patient anatomy, implants, components of the CAS system 100, etc.) into a coordinate system used by a process running on a surgical controller and/or computer device of the robotic system 104. As is well-known, a coordinate transform process may include any suitable transformation technique, such as, for example, rigid-body transformation, non-rigid transformation, affine transformation, and the like.

Additionally, the CAS system 100 (e.g., via the computing system) may include modeling capabilities such that the CAS system 100 may create one or more models of physical objects in virtual space. For example, the CAS system 100 may create models of patient anatomy, prosthetic implants, components of the CAS system 100, etc. In one embodiment, the CAS system 100 may create one or more models based on imaging data (e.g., from an MRI, from a CT scan, from an ultrasound, etc.). In another embodiment, the CAS system 100 may create one or more models based on data from a trackable probe. For example, the surgeon may contact and move a trackable probe over the surface of an implant and/or patient anatomy, and navigation system 101 may determine a pose and movement of the trackable probe over the contacted surfaces. The computing system 102 may then then create a model of the contacted surfaces based on data from the navigation system regarding the trackable probe. In a third embodiment, the CAS system 100 may select one or more models from a database of models (e.g., a database stored in a memory of the computing system 102). In a fourth embodiment, the CAS system 100 may select one or more models from a database of models and modify the model(s) based on imaging data, based on data from a trackable probe, etc.

Registration (e.g., registering one or more objects in physical space to virtual space) may include any known registration technique, such as, for example, image-to-image registration (e.g., monomodal registration where images of the same type or modality, such as fluoroscopic images or magnetic resonance images, are registered and/or multimodal registration where images of different types or modalities, such as MRI and CT, are registered), image-to-physical space registration (e.g., image-to-patient registration where a digital data set of a patient's anatomy obtained by conventional imaging techniques is registered with the patient's actual anatomy), combined image-to-image and image-to-physical-space registration (e.g., registration of preoperative CT and MRI images to an intraoperative scene), and/or registration using a video camera with tracking capabilities to create an initial model. For example, in some embodiments, the CAS system 100 includes video camera and various trackers to track one or more objects in physical space. The computing system 102 receives a scan of patient anatomy, obtains a model based on the scan, and registers the one or more objects in physical space to the model. In one embodiment, the computing system 102 creates an initial 3D model and automatically registers one or more physical objects to the 3D model (e.g., the computing system 102 uses a video camera to register a 3D model corresponding to a CT scan).

In various embodiments, registration with respect to the robotic-assisted debridement procedures described herein includes determining or digitizing an area to be debrided, for example, an area to be irrigated (e.g., an irrigation area or a lavage zone) with an irrigation fluid, such as bactericidal solutions, nanoparticle solutions, biofilm inhibiting agents, and/or antibiotics using the above-described registration and/or tracking methods. In one embodiment, the irrigation area is determined by using a pre-operative scan of the infected implant and surrounding tissue. In another embodiment, the irrigation area is digitized through the use of a trackable probe. The surgeon touches the probe to the patient anatomy and/or to the infected implant to trace the irrigation area (e.g., trace a perimeter of the irrigation area). The navigation system 101 tracks the probe (e.g., using markers on the probe or using the geometry of the probe), and the CAS system 100 uses the data from the navigation system 101 to digitize the irrigation area.

As noted above, the computing system 102 may execute one or more processes relating to registration. Accordingly, the computing system 102 may be communicably coupled to the navigation system 101 and may be configured to receive data from the navigation system 101. Based on the received navigation data, computing system 102 may determine the position and orientation associated with one or more registered features of the surgical environment, such as surgical tool 110 or portions of the patient's anatomy. Computing system 102 may further include modeling software used during various procedures. Furthermore, computing system 102 may include surgical planning and surgical assistance software that may be used by a surgeon or surgical support staff during the surgical procedure. For example, during a debridement procedure, computing system 102 may display images related to the procedure on one or both of the display devices 103a and 103b.

Figure 2:
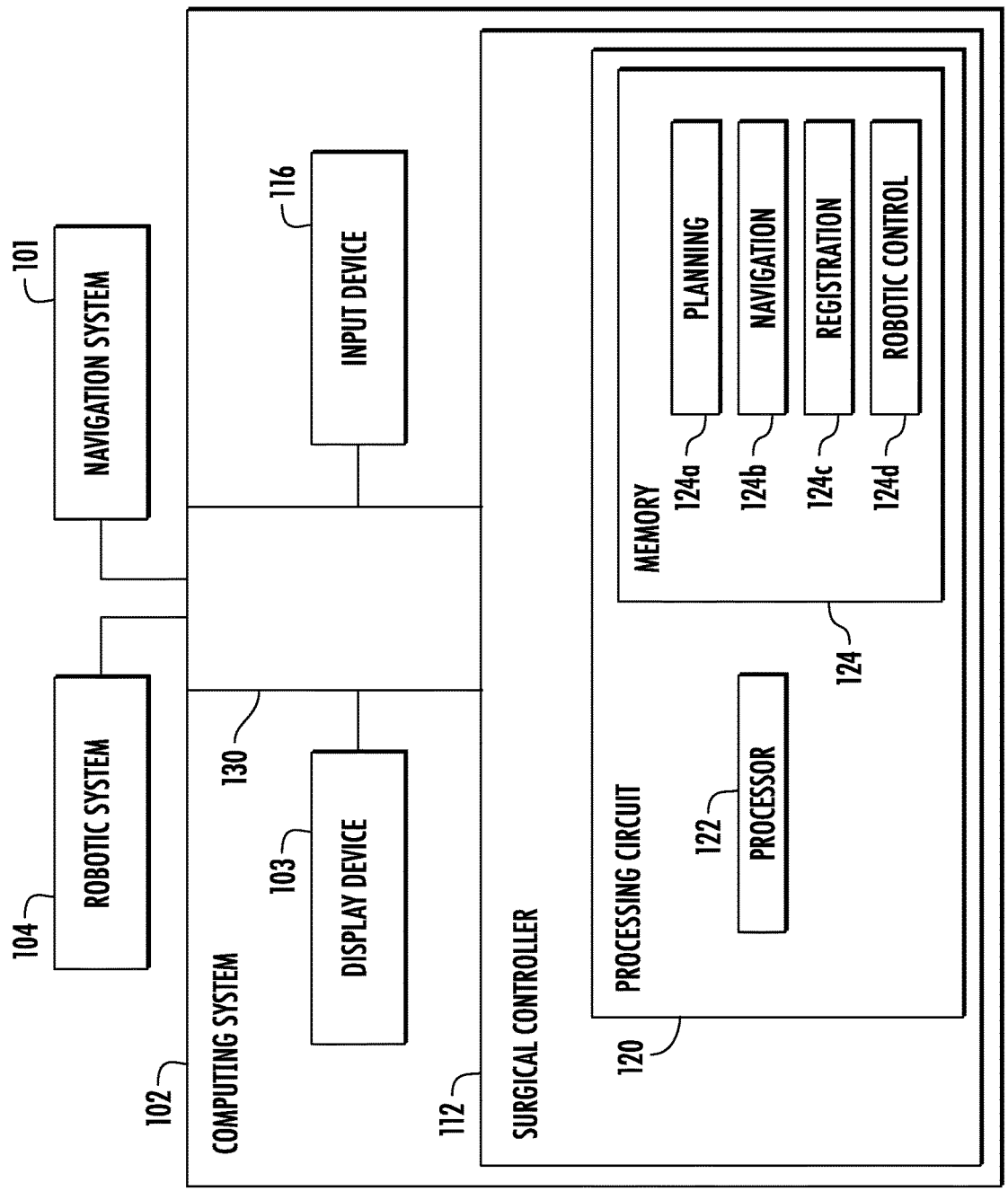
FIG. 2 illustrates a block diagram of a computing system, according to an exemplary embodiment.

Computing system 102 (and/or one or more constituent components of CAS system 100) may include hardware and software for operation and control of the CAS system 100. Such hardware and/or software is configured to enable the CAS system 100 to perform the techniques described herein. As an illustration, FIG. 2 shows a block diagram of the computing system 102 according to an exemplary embodiment. The computing system includes a surgical controller 112, a display device 103 (e.g., display devices 103a and 103b), and an input device 116.

The surgical controller 112 may be any known computing system but is preferably a programmable, processor-based system. For example, the surgical controller 112 may include a microprocessor, a hard drive, random access memory (RAM), read only memory (ROM), input/output (I/O) circuitry, and any other known computer component. The surgical controller 112 is preferably adapted for use with various types of storage devices (persistent and removable), such as, for example, a portable drive, magnetic storage, solid state storage (e.g., a flash memory card), optical storage, and/or network/Internet storage. The surgical controller 112 may comprise one or more computers, including, for example, a personal computer or a workstation operating under a suitable operating system and may include a graphical user interface ("GUI").

Still referring to FIG. 2, in an exemplary embodiment, the surgical controller 112 includes a processing circuit 120 having a processor 122 and memory 124. Processor 122 can be implemented as a general purpose processor executing one or more computer programs to perform actions by operating on input data and generating output. The processes and logic flows can also be performed by, and apparatus can also be implemented as, special purpose logic circuitry, e.g., a field programmable gate array ("FPGA") or an application specific integrated circuit ("ASIC"), a group of processing components, or other suitable electronic processing components. Generally, a processor will receive instructions and data from a read only memory or a random access memory or both.

Memory 124 (e.g., memory, memory unit, storage device, etc.) comprises one or more devices (e.g., RAM, ROM, Flash-memory, hard disk storage, etc.) structured for storing data and/or computer code for completing or facilitating the various processes described in the present application. Memory 124 may be or include volatile memory or non-volatile memory. Memory 124 may include database components, object code components, script components, or any other type of information structure for supporting the various activities described in the present application. According to an exemplary embodiment, memory 124 is communicably connected to processor 122 and includes instructions (e.g., computer code) for executing one or more processes described herein. The memory 124 may contain a variety of modules, each capable of storing data and/or computer code related to specific types of functions. In one embodiment, memory 124 contains several modules related to surgical procedures, such as a planning module 124a, a navigation module 124b, a registration module 124c, and a robotic control module 124d.

Alternatively, or in addition, the computer program instructions can be encoded on an artificially generated propagated signal (e.g., a machine-generated electrical, optical, or electromagnetic signal) that is generated to encode information for transmission to a suitable receiver apparatus for execution by a data processing apparatus. A computer storage medium can be, or be included in, a computer-readable storage device, a computer-readable storage substrate, a random or serial access memory array or device, or a combination of one or more of said devices and/or substrates. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, flash drives, or other storage devices). Accordingly, the computer storage medium may be tangible and non-transitory.

A computer program (also known as a program, software, software application, script, or code) can be written in any form of programming language, including compiled or interpreted languages, or declarative or procedural languages. A computer program can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Generally, a computer, such as computing system 102, will also include, or be operatively coupled to receive data from or transfer data to, or both, one or more mass storage devices for storing data (e.g., magnetic, magneto optical disks, or optical disks). However, a computer need not have such devices. Moreover, a computer can be embedded in another device, e.g., a mobile telephone, a tablet, a personal digital assistant ("PDA"), a mobile audio or video player, a game console, a Global Positioning System ("GPS") receiver, or a portable storage device (e.g., a universal serial bus ("USB") flash drive), to name just a few. Devices suitable for storing computer program instructions and data include all forms of non-volatile memory, media and memory devices, including by way of example semiconductor memory devices (e.g., EPROM, EEPROM, and flash memory devices), magnetic disks (e.g., internal hard disks or removable disks), magneto optical disks, and CD ROM and DVD-ROM disks. Further, the processor 122 and the memory 124 can be supplemented by, or incorporated in, special purpose logic circuitry.

Additionally, in various embodiments, the computing system 102 is implemented as a computing system that includes a back end component (e.g., as a data server), includes a middleware component (e.g., an application server), or includes a front end component (e.g., a client computer having a GUI or a Web browser through which a user can interact with an embodiment of the subject matter described in this specification), or that includes any combination of one or more such back end, middleware, or front end components. The components of the computing system 102 can be interconnected by any form or medium of digital data communication (e.g., a communication network).

Referring to the embodiment of CAS system 100 depicted in FIG. 2, the surgical controller 112 further includes a communication interface 130. The communication interface 130 of the computing system 102 is coupled to a computing device (not shown) of the robotic system 104 via an interface and to the navigation system 101 via an interface. The interfaces can include a physical interface and/or a software interface. A physical interface of the communication interface 130 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.). A software interface may be resident on the surgical controller 112, the computing device (not shown) of the robotic system 104, and/or the navigation system 101. Furthermore, in some embodiments, the surgical controller 112 and the computing device (not shown) of the robotic system 104 are the same computing device. The software may also operate on a remote server, be housed in the same building as the CAS system 100, or be housed at an external server site.

Computing system 102 also includes display device 103. The display device 103 is a visual interface between the computing system 102 and the user. The display device 103 is connected to the surgical controller 112 and may be any device suitable for displaying text, images, graphics, and/or other visual output. For example, the display device 103 may include a standard display screen, a touchscreen, a wearable display (e.g., eyewear such as glasses or goggles), a projection display, a head-mounted display, a holographic display, and/or any other visual output device. In certain embodiments, the display may be incorporated into a shield that is part of the surgeon's sterile gown. The display device 103 may be disposed on or near the surgical controller 112 (e.g., on the cart as shown in FIG. 1) or may be remote from the surgical controller 112 (e.g., mounted on a stand with the navigation system 101). The display device 103 is preferably adjustable so that the user can position/reposition the display device 103 as needed during a surgical procedure. For example, the display device 103 may be disposed on an adjustable arm (not shown) or to any other location well-suited for ease of viewing by the user. As shown in FIG. 1 there may be more than one display device 103 in the CAS system 100 (e.g., display devices 103a and 103b).

The display device 103 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), constraint data (e.g., axes, articular surfaces, etc.), representations of implant components, digital or video images, registration information, calibration information, patient data, user data, measurement data, software menus, selection buttons, status information, and the like.

In addition to the display device 103, the computing system 102 may include an acoustic device (not shown) for providing audible feedback to the user. The acoustic device is connected to the surgical controller 112 and may be any known device for producing sound. For example, the acoustic device may include speakers and a sound card, a motherboard with integrated audio support, and/or an external sound controller. In operation, the acoustic device may be adapted to convey information to the user. For example, the surgical controller 112 may be programmed to signal the acoustic device to produce a sound, such as a voice synthesized verbal indication "DONE," to indicate that a step of a procedure (e.g., a step of irrigating an infected implant and/or infected tissue) is complete.

To provide for other interaction with a user, embodiments of the computing system 102 may have an input device 116 that enables the user to communicate with the CAS system 100. As shown in FIG. 2, the input device 116 is connected to the surgical controller 112, and the input device 116 may include any device enabling a user to provide input to a computer. For example, the input device 116 can be any known input device, such as a keyboard, a mouse, a trackball, a touchscreen, a touchpad, voice recognition hardware or software, dials, switches, buttons, a trackable probe, a foot pedal, a remote control device, a scanner, a camera, a microphone, and/or a joystick. Other kinds of devices can be used to provide for interaction with a user as well. For example, the input device 116 may also serve as an output device and provide feedback to the user as any form of sensory feedback (e.g., visual feedback, auditory feedback, or tactile feedback) and receive input from the user in any form, including acoustic, speech, or tactile input. In addition, the computing system 102 can interact with a user by sending documents to and receiving documents from a device that is used by the user, for example, by sending web pages to a web browser on a user's client device in response to requests received from the web browser.

General surgical planning and navigation to carry out the exemplary methods described above, including control and feedback as described in connection with CAS system 100, may be performed by a computerized surgical system such as that described in U.S. Pat. No. 8,010,180 "Haptic Guidance System and Method" to Quaid et al., which is incorporated herein by reference in its entirety.

Furthermore, it should be appreciated that CAS system 100 described herein, as well as the methods and processes described herein, may be applicable to many different types of implant debridement procedures. Although certain disclosed embodiments may be described herein with reference to methods, systems, and procedures for irrigating a knee implant, the concepts and methods described herein may be applicable to other types debridement procedures, such as hip, shoulder, ankle, and implant debridement procedures. Further, the CAS system 100 may include additional elements or fewer elements than those described above to aid in surgery (e.g., a surgical bed, etc.).

Robotic-Assisted Debridement

Figure 3A:
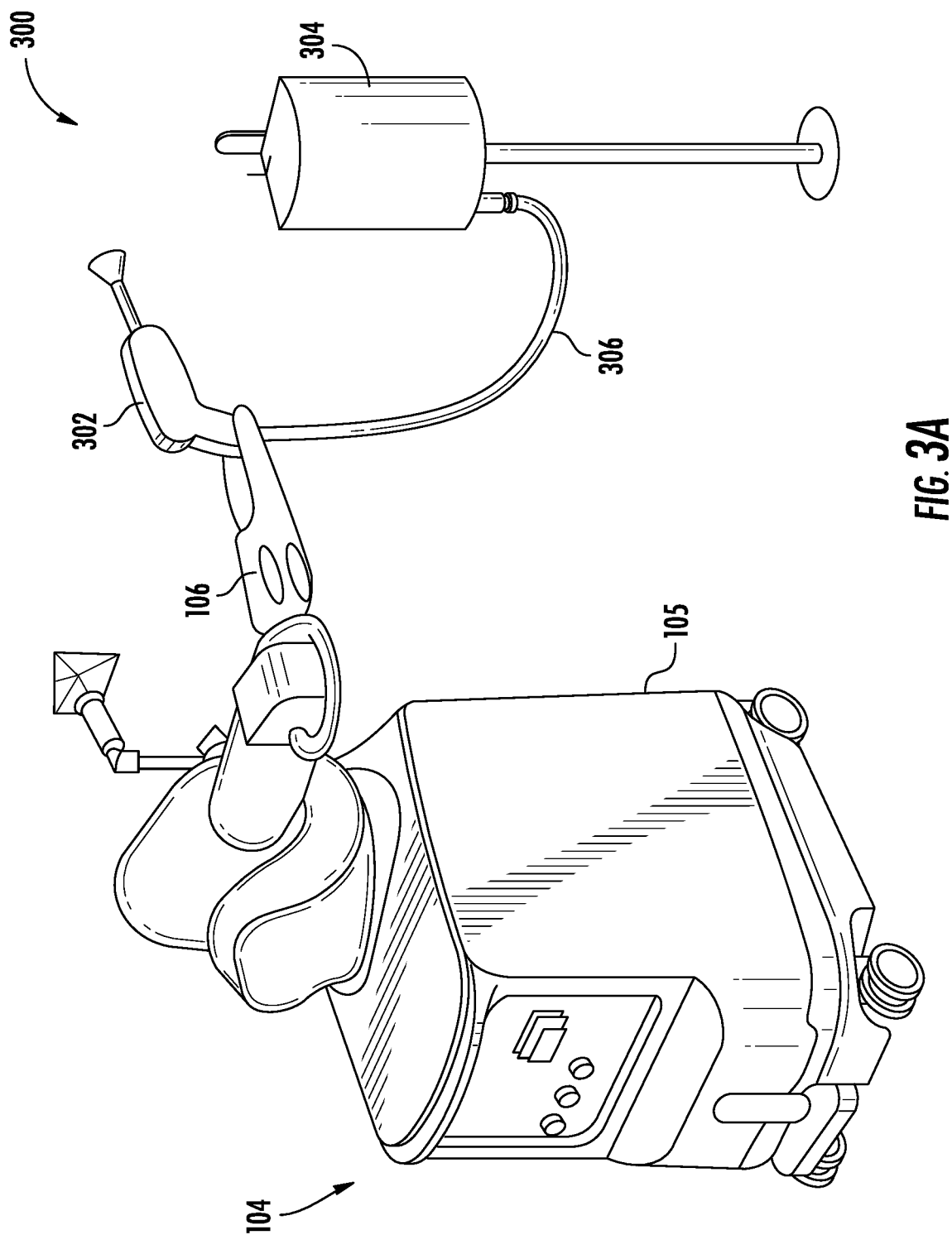
FIG. 3A illustrates a perspective view of a robotic system with irrigation components according to an exemplary embodiment.

FIG. 3A provides a schematic diagram of the robotic system 104 coupled to an irrigation system 300. As shown in FIG. 3A, surgical tool 110 is an irrigation tool 302 coupled to the articulated arm 106. In some embodiments, the irrigation tool 302 is a pulsed lavage hydro jet configured to create and direct a fluid stream. The pulsed lavage hydro jet may include an elongated nozzle for directing fluids out of the hydro jet (e.g., as shown in FIG. 3A). Alternatively, the pulsed lavage hydro jet may include a shorter nozzle or a nozzle having a shield. The irrigation tool 302 receives irrigation fluid from an irrigation source 304 via tubing 306. In some embodiments, the irrigation source 304 may be coupled to or incorporated in the robotic system 104. The irrigation fluid may be, for example, a bactericidal solution, nanoparticle solution, biofilm inhibiting agent, antibiotic, and/or any other cleaning or lavage fluid appropriate for infection treatment. Additionally, some embodiments of the irrigation system 300 may include a suction tool (not shown) coupled to the irrigation tool 302 or separate from the irrigation tool 302 for removing fluids that are dispensed from the irrigation tool 302.

Figure 3B:
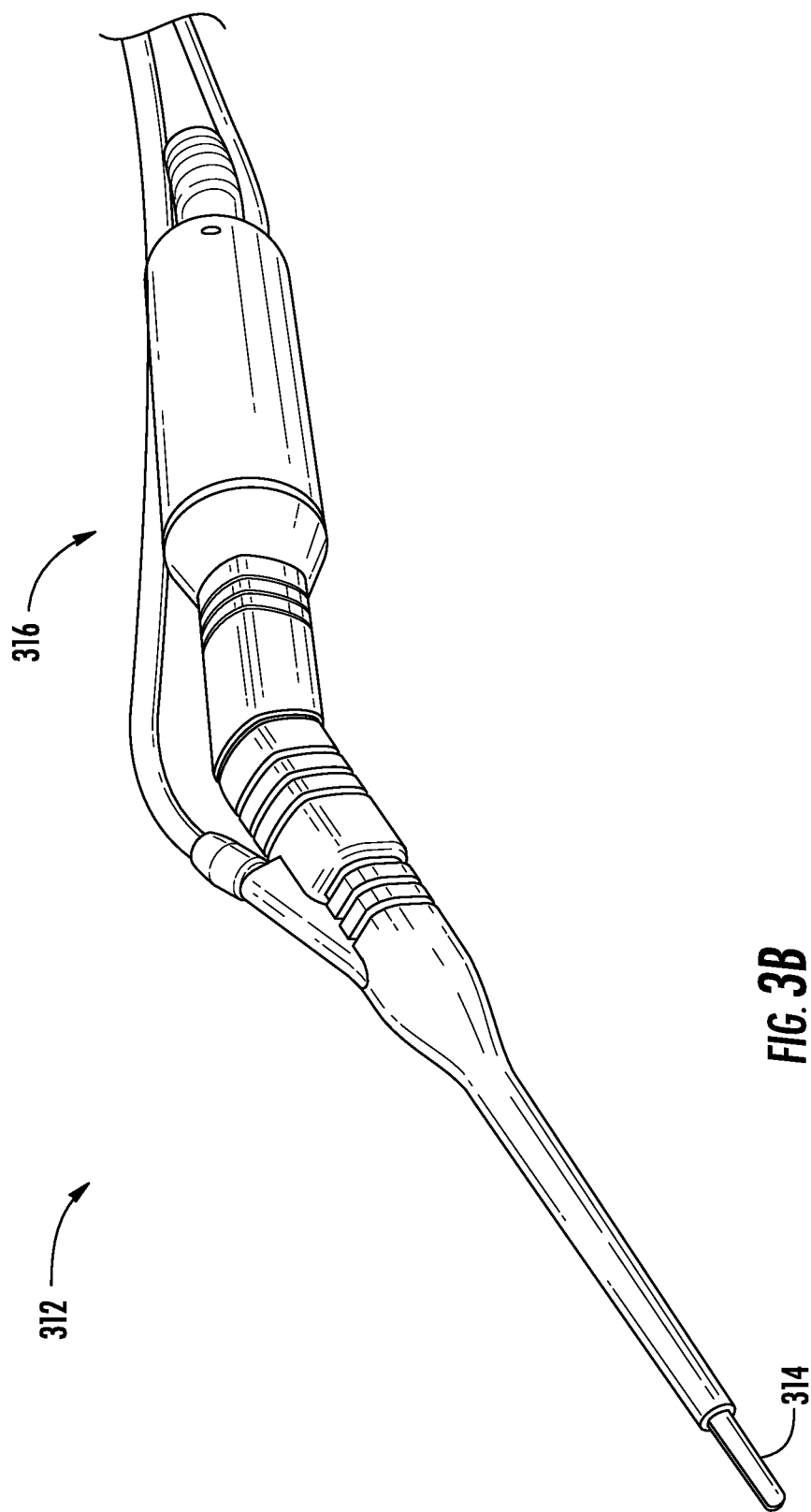
FIG. 3B illustrates an ultrasonic tool for use with the robotic system of FIG. 3A, according to an exemplary embodiment.

In other embodiments, additionally or alternatively, the irrigation tool 302 may be an ultrasonic tool, such as ultrasonic tool 312 shown in FIG. 3B. For example, the ultrasonic tool 312 may include a probe that uses low frequency, high intensity ultrasound to cause the tip 314 of the probe to vibrate. In some embodiments, the ultrasonic frequency provided by the ultrasonic tool 312 is between 25 kHz and 35 kHz. The ultrasonic tool 312 may use longitudinal vibration and/or torsional vibration to emulsify tissue with improved precision. The tip 314 of the probe may be any variation of soft tissue, implant, or bone scouring tips available or able to be modified for debridement. The ultrasonic tool 312 may include an angled body 316, such as the embodiment shown in FIG. 3B, or may have a straight body. The ultrasonic tool 312 may be part of an ultrasonic system which provides ultrasonic power, suction, and irrigation.

When the vibrating tip 314 contacts the infected site, the vibration causes micro-sized gas bubbles in the fluids at the infected site, which implode and destroy nearby tissue and bacteria without damaging the bone or any bone cement attaching the implant to the bone. Once the ultrasonic tool 312 has fragmented and emulsified infected tissue and bacteria, the tool 312 may use aspiration to remove the tissue from the area. In this way, the ultrasonic tool 312 is capable of debriding the infected area in a manner that removes bacteria and infected tissue without the use of irrigation fluid or in addition to the use of irrigation fluid, such as bactericidal solutions, nanoparticle solutions, biofilm inhibiting agents, and/or antibiotics. Using ultrasonic tools for debridement can damage (e.g., scratch) an implant component if the ultrasonic tip comes into contact with the component, however, controlling the ultrasonic tool 312 with a robotic-assisted system guides the ultrasonic tool 312 and prevents contact with the component, thereby improving effectiveness and efficiency of debridement, while minimizing the risk of damage to the implant component. It is to be understood that references elsewhere herein to the irrigation tool 302 can also apply to the ultrasonic tool 312, which can be used interchangeably with or in addition to the irrigation tool 302, and in a similar way.

Similar to the surgical tool 110, a surgeon can manipulate the irrigation tool 302 by grasping and moving the articulated arm 106 and/or the irrigation tool 302. Alternatively, the surgeon can manipulate the irrigation tool 302 by an input/output device (not shown) to move the articulated arm 106 and/or the irrigation tool 302. It should be understood, however, that the irrigation tool 302 an example irrigation tool to be used as part of an irrigation system and that other embodiments of irrigation tools or irrigation systems may be used with the systems and methods described herein.

In some embodiments, the irrigation tool 302 is not coupled to the articulated arm 106 and is instead manually supported and moved by the surgeon. The navigation system 101 is used to track movement of the irrigation tool 302 while it is being manually manipulated. The navigation system 101 for a manually manipulated irrigation tool 302 may be any system as described above, including for example, an optical tracking system or a passive jointed mechanical arm.

Figure 4A:
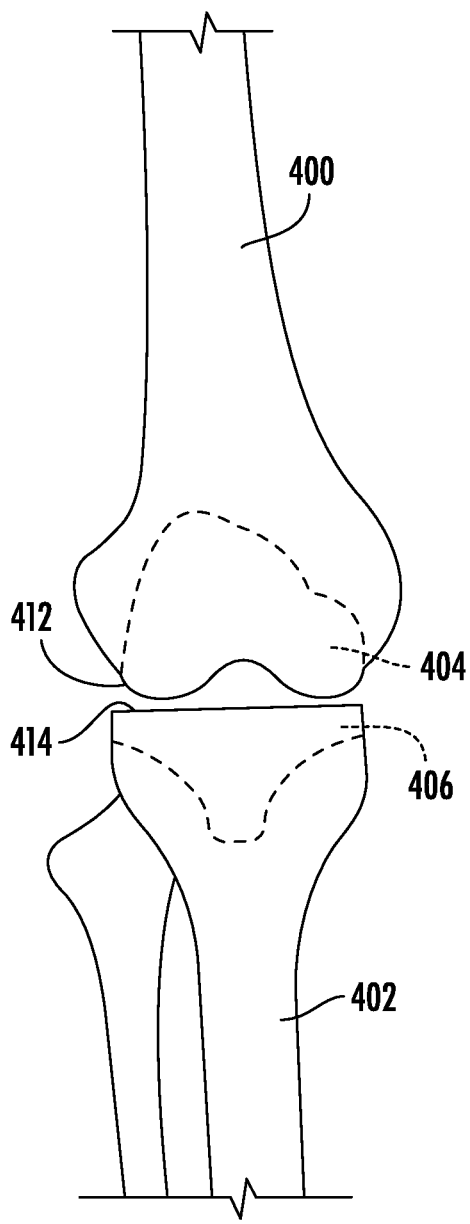
FIGS. 4A and 4B illustrate a femur, a tibia, a femoral implant, and a tibial implant, according to an exemplary embodiment.
Figure 4B:
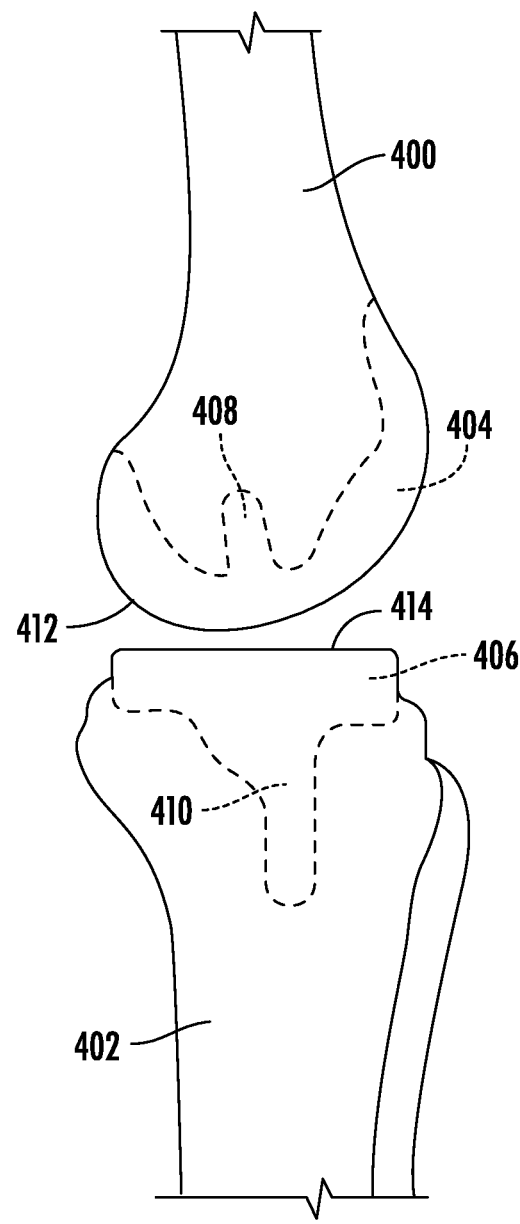

As described in further detail below, a surgeon can use the irrigation system 300 with the CAS system 100 to debride an infected implant, as well as the surrounding tissues, to treat the infected implant. Alternatively, the surgeon can use the irrigation system 300 with the CAS system 100 to irrigate infected tissues after an infected implant has been removed. An implant positioned in the knee is used herein to describe the process of using the irrigation system 300 and the CAS system 100 to treat an infected implant and/or infected tissue, though it should be understood that the irrigation system 300 and the CAS system 100 may be used to treat implants in other bones or joints, including but not limited to shoulder, wrist, spine, and ankle implants. Accordingly, FIGS. 4A and 4B illustrate views of a femur 400 and a tibia 402 with a femoral implant 404 and a tibial implant 406, respectively, according to an example embodiment. As shown, the femoral implant 404 includes projections, such as a peg 408 extending into the femur 400, and the tibial implant 406 includes, for example, a keel 410. In FIGS. 4A and 4B, the dashed lines of the femoral implant 404 and the tibial implant 406 denote interior surfaces of the implants 404 and 406 (e.g., surfaces that are cemented to the femur 400 and the tibia 402, respectively). The solid lines of the implants 404 and 406 denote articulating surfaces of the implants 404 and 406 (e.g., exposed surfaces that articulate together to form the joint replacement for the femur 400 and the tibia 402). Thus, as shown in FIGS. 4A and 4B, the femoral implant 404 includes a femoral articulating surface 412 and the tibial implant 406 includes a tibial articulating surface 414.

At times, the femoral implant 404 and/or the tibial implant 406 will become infected once implanted in the femur 400 and tibia 402 of an implant. For example, a biofilm may adhere to the femoral articulating surface 412 of the femoral implant 404 and/or the tibial articulating surface 414 of the tibial implant 406. If the femoral implant 404 and/or the tibial implant 406 become infected, a surgeon must decide whether to remove the infected implants 404 and/or 406. In the case of an early infection, however, the surgeon can treat the infection without removing the implants 404 and/or 406 by thoroughly irrigating the implants 404 and 406 and debriding the surrounding tissues with an irrigation fluid. Alternatively, if the infection is more serious, the surgeon can remove the infected implants 404 and/or 406, clean the infected implants 404 and/or 406, and use the irrigation system 300 with the CAS system 100 to debride the infected patient tissues. The surgeon can then re-insert the cleaned implants 404 and/or 406, or new implants, into the patient.

In various embodiments, the implants 404 and 406 and/or the infected patient tissues may be debrided with an irrigation fluid, such as bactericidal solutions, nanoparticle solutions, biofilm inhibiting agents, antibiotics, and/or any other cleaning or lavage fluid appropriate for infection treatment. The debridement should be able to, for example, penetrate and destroy a biofilm that has formed on the femoral implant 404 and/or the tibial implant 406.

As discussed above, while implant debridement can be done without computer guidance, such debridement relies on the surgeon's ability to cover the entire infected area. Accordingly, the surgeon may instead use the CAS system 100 described herein to generate a debridement plan that will cover all of the affected areas that need to be irrigated or otherwise debrided. Beneficially, generating a plan with the CAS system 100 ensures that the entirety of the affected areas are debrided. Further, the CAS system 100 is able to monitor the debridement of the affected areas, based on movement of the articulated arm 106 and/or using information from tracking system 101, for example for a manually manipulated tool, to confirm that the affected areas are completely debrided.

Figure 5:
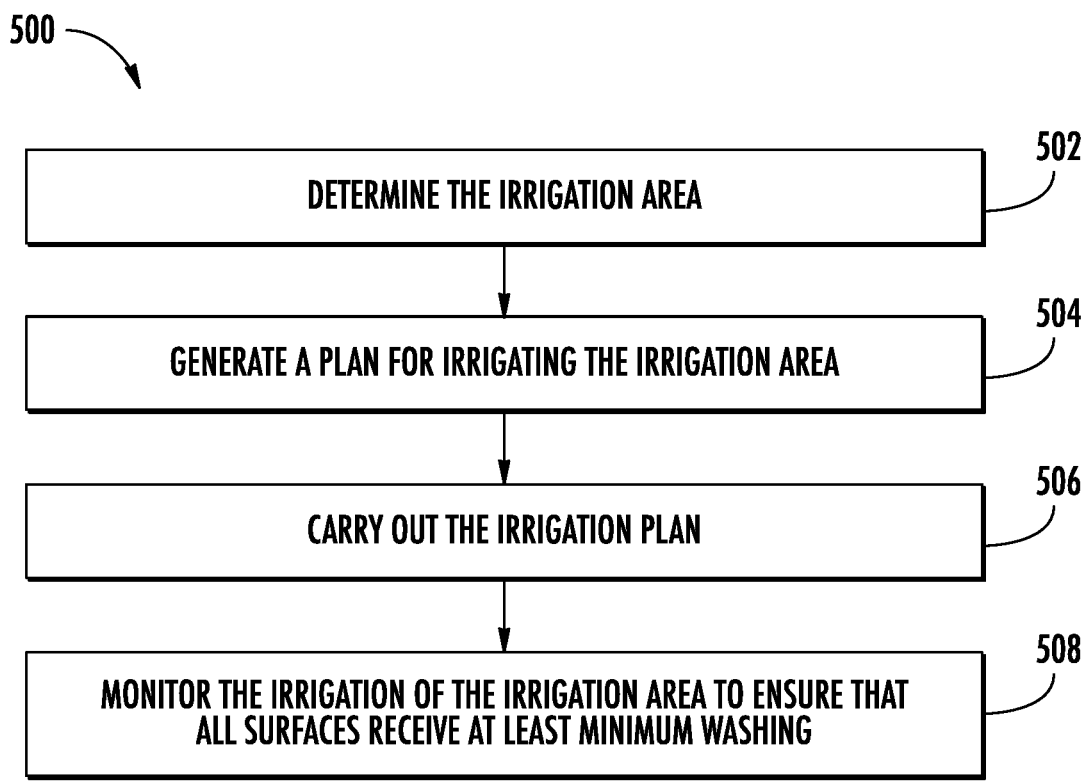
FIG. 5 is a flow chart of a method of performing a robotic-assisted debridement procedure, according to an exemplary embodiment.

FIG. 5 illustrates a method 500 of preparing a debridement plan and debriding an infected prosthetic device, such as femoral implant 404 and tibial implant 406, and/or infected patient tissues according to an example embodiment. To begin with, the area to be debrided is determined, in this embodiment, this comprises determining the irrigation area (502). In some embodiments, the surgeon may identify the infected areas visually. Alternatively, in other embodiments, the surgeon may identify the infected areas with the aid of infection detection systems and methods. For example, the patient may consume or be injected with an imaging agent, such as a fluorescent imaging agent composed of antibodies that bind to proteins in the blood. The antibodies may accumulate in the infection site because of increased blood flow due to inflammation caused by the infection or because the types of proteins the antibodies bind to have accumulated at the source of the infection (e.g., the proteins are on white blood cells accumulating at the infection site). Alternatively, the imaging agent may be composed of antibodies that bind to bacteria common in biofilms and accumulate at the infection site because of the presence of the biofilm bacteria at the site. In certain arrangements, the fluorescent imaging agent may include different antibodies that bind to different proteins (e.g., with some antibodies binding to blood cells, some binding to biofilm bacteria, etc.). Next, the imaging agent is illuminated using a fluorescent imaging system to label the infected areas, allowing the physician to visualize the infected areas and use the robot to debride the infected areas. Alternatively, biofilms may be stained using solutions or dyes (for example, methylene blue, congo red, etc.) which can also allow the physician to visualize the area.

In certain embodiments, the irrigation area is then digitizing. With reference to FIGS. 4A and 4B, if the infection is not severe, the irrigation area may include the femoral articulating surface 412, the tibial articulating surface 414, the cement areas for the implants 404 and 406, and the tissue surrounding the femoral implant 404 and the tibial implant 406, such as the areas of the femur 400 and tibia 402 and the connective tissue adjacent to the implants 404 and 406. If the infection is more severe, the surgeon may first remove the infected implants 404 and/or 406 before carrying out the method 500, and the irrigation area may include the tissues at and surrounding the site of the removed implants 404 and/or 406. In one embodiment, the irrigation area is digitized using a tracked probe. For example, the surgeon touches the tracked probe to the perimeter of the area to be irrigated (e.g., the perimeter of the femoral articulating surface 412 and the tibial articulating surface 414 or the infected tissues at or surrounding the implant sites for the femoral implant 404 and/or the tibial implant 406). In another embodiment, the irrigation area is determined using a pre-operative scan. For example, the irrigation area is imaged using any of a variety of imaging techniques (e.g., CT, MRI, ultrasound, video camera, etc.). Once imaged, a model of the anatomy identifying the irrigation area may be created using the computing system 102 according to the modeling systems and methods described above. In further embodiments, the robotic device may be able to automatically detect labeled or stained areas indicating infection and remove the areas without requiring separate imaging or digitizing the determined areas.

After the irrigation area is determined, a plan for irrigating the irrigation area is generated (504). In various embodiments, robotic planning software executed using the CAS system 100 (e.g., executed using the computing system 102) generates the irrigation plan. The robotic planning software bases the irrigation plan on the determined irrigation area and, in some cases, on other constraints of the CAS system 100. For example, the robotic planning software may take into account the properties and constraints of the irrigation tool 302 when generating the irrigation plan, such as the range, speed, and pressure of hydro jet spray or the speed of ultrasonic debridement. The irrigation plan is intended to guarantee that all surfaces of the prosthetic implant (e.g., the femoral articulating surface 412, the tibial articulating surface 414, and the bone cement adhering the implants 404 and 406 to the femur 400 and tibia 402, respectively) and/or the tissues at the implant site of a removed prosthetic implant (e.g., the areas of the femur 400 and tibia 402 and the connective tissues surrounding the implantation sites for the femoral implant 404 and the tibial implant 406) in the irrigation area are irrigated. The irrigation plan may be a pre-determined plan that is associated with a particular implant, and may be obtained from a database. The pre-determined plan may be customized by a surgeon based on the actual characteristics of the patient's anatomy and on the infection state of the implant and/or surrounding tissues. In other embodiments, the irrigation plan may be completely customized.

Once created, the surgeon carries out the debridement plan, such as the irrigation plan, using the irrigation system 300 coupled to the robotic system 104 (506). In some embodiments, the surgeon carries out the irrigation plan aided by the CAS system 100. In one example, the robotic system 104 provides haptic guidance to the surgeon to guide the surgeon in completing the irrigation plan (e.g., by providing resistance or a vibration when the surgeon is straying from the irrigation plan). In another example, the CAS system 100 aids with carrying out the irrigation plan by tracking and monitoring movement of the irrigation tool 302 where the tool 302 is not coupled to an articulated arm. In other embodiments, however, the robotic system 104 carries out the irrigation plan autonomously. Additionally, the surgeon may be able to select between options of carrying out the irrigation plan with aid from the CAS system 100 or having the robotic system 104 carry out the irrigation plan autonomously.

Additionally, in various embodiments, the robotic system 104 may adjust parameters of the irrigation tool 302 or ultrasonic tool 312 to ensure complete debridement of the irrigation area. For example, the robotic system 104 may adjust the speed and the pressure of the spray from the irrigation tool 302 and/or the parameters of the ultrasonic debridement tool 312 to ensure complete cleaning of all surfaces. As another example, the robotic system 104 may adjust the speed and the pressure of the spray from the irrigation tool 302 and/or the parameters of the ultrasonic debridement tool 312 depending on the type of surface that is being cleaned (e.g., provide less pressure when patient tissues are being cleaned as opposed to implant surfaces). Furthermore, in some embodiments, the robotic system 104 and/or the surgeon may use an ultraviolet ("UV") light component to target bacterial biofilms on the infected implants and thereby disinfect the implants. The UV light component may be included as part of the irrigation tool 302, may be included as a separate instrument coupled to the robotic system 104, or may be included on a separate robotic or surgical system.

During the debridement of the infected implant according to the debridement plan, the CAS system 100 monitors the progress of the debridement to ensure that all surfaces receive at least minimum debridement. For example, the navigation system 101 may monitor the movement of the irrigation tool 302 with respect to registered patient anatomy and registered implants such that the CAS system 100 may determine which areas of the irrigation area have received debridement (e.g., based on the size, pressure, etc. of the spray from the irrigation tool 302 and/or ultrasonic debridement tool 312).

In embodiments where the CAS system 100 aids the surgeon in carrying out the debridement plan, the CAS system 100 may provide feedback to the surgeon based on the monitoring. For example, the robotic system 104 may provide haptic guidance to the surgeon to guide the surgeon toward sections of the irrigation area that need additional debridement. In another example, the CAS system 100 may display sections of the irrigation area that need additional debridement on the displays 103*a* and/or 103*b* or on a separate display (e.g., on the shield that is part of the surgeon's sterile gown). The CAS system 100 may show sections that need additional debridement in one color and transition the sections to a second color once they have received at least minimum debridement. In a third example, the CAS system 100 may provide oral guidance to the surgeon to guide the surgeon towards sections that need additional debridement. Conversely, in embodiments where the robotic system 104 carries out the plan autonomously, the CAS system 100 may follow the debridement plan based on the monitoring until all of the irrigation area has received at least minimum debridement. Additionally, in various embodiments, the computing system 102 may update the debridement plan if it determines that some sections of the irrigation area are not receiving sufficient debridement under the original irrigation plan.

In cases where the infection was determined to be more severe and the implant(s) (e.g., the femoral implant 404 and/or the tibial implant 406 were removed), the surgeon may use the CAS system 100 to re-implant new or the removed implant(s) in the patient. For example, the surgeon may replace the irrigation tool 302 with a tool adapted for re-implantation, formulate a re-implantation surgical plan with the CAS system 100, and follow the surgical plan to re-implant the removed or new implant(s).

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. As described herein, embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although a specific order of method steps may be described, the order of the steps may differ from what is described. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish any connection steps, processing steps, comparison steps, and decision steps.

What is claimed is:

1. A method for irrigating an infected implant area, the method comprising:
    determining, by a processing circuit associated with a computer, an irrigation area to be irrigated, the irrigation area including at least a surface of an implant and patient tissue;
    irrigating, by an irrigation system, the irrigation area with a spray of an irrigation fluid;
    monitoring, by the processing circuit, debridement of the irrigation area via the spray of the irrigation fluid; and
    controlling, by the processing circuit, the irrigation system to automatically adjust a speed of the spray of the irrigation fluid from the irrigation system to provide a first speed when debridement is of the surface of the implant and a second speed when the debridement is of the patient tissue.

2. The method of claim 1, the method further comprising:
    providing a trackable probe configured to contact the surface of the implant and the patient tissue;
    tracking, by a navigation system associated with the computer, a position of the probe; and
    generating, by the navigation system, information relating to the irrigation area based on the position of the probe;
    wherein determining the irrigation area comprises digitizing, by the processing circuit, the irrigation area based on the information relating to the irrigation area.

3. The method of claim 1, the method further comprising:
    receiving, by the processing circuit, images of the irrigation area;
    wherein determining the irrigation area is based on the images of the irrigation area.

4. The method of claim 1, wherein the irrigation area includes at least the surface of the implant, bone cement for the implant, and the patient tissue.

5. The method of claim 1, the method further comprising:
    removing the implant; and
    after the entirety of the irrigation area receives at least minimum debridement, implanting a new implant;

wherein the patient tissue of the irrigation area surrounds a site of the implant.

6. The method of claim 1, wherein the irrigation fluid is an antibiotic.

7. The method of claim 1, further comprising irrigating the irrigation area according to an irrigation plan by providing guidance for carrying out the irrigation plan to a surgeon.

8. The method of claim 7, the method further comprising:
providing a haptic system; and
irrigating the irrigation area according to the irrigation plan comprises using the haptic system to provide haptic feedback on the irrigation system based on the irrigation plan while the irrigation system irrigates the irrigation area.

9. The method of claim 7, wherein the guidance comprises displaying, on a display, an image of a section of the irrigation area that has not received at least minimum irrigation.

10. The method of claim 1, wherein irrigating the irrigation area comprises tracking, using a navigation system associated with the computer, movement of an irrigation tool of the irrigation system while a surgeon manually manipulates the irrigation tool while irrigating the irrigation area.

11. The method of claim 1, wherein irrigating the irrigation area comprises controlling a robotic system to autonomously irrigate the irrigation area.

12. The method of claim 1, further comprising:
providing an ultraviolet light component; and
using the ultraviolet light component to disinfect the irrigation area.

13. A method for irrigating an irrigation area comprising a surface of an implant and patient tissue, the method comprising:
providing a spray of irrigation fluid from an irrigation tool to the irrigation area; and
automatically adjusting, by processing circuitry, a speed of the spray of the irrigation fluid from the irrigation tool by providing a first spray speed when spraying the surface of the implant and a second spray speed when spraying the patient tissue.

14. The method of claim 13, the method further comprising:
receiving, by the processing circuitry, images of the irrigation area and determining the irrigation area based on the images of the irrigation area.

15. The method of claim 13, wherein the irrigation area further comprises bone cement for the implant.

16. The method of claim 13, the method further comprising:
planning removal of the implant; and
planning re-implantation of a new implant;
wherein the patient tissue of the irrigation area surrounds a site of the implant.

* * * * *